United States Patent
Liu et al.

(10) Patent No.: US 7,362,448 B1
(45) Date of Patent: Apr. 22, 2008

(54) CHARACTERIZING RESIDUE ON A SAMPLE

(75) Inventors: Zhuan Liu, Fremont, CA (US); Sangbong Lee, San Leandro, CA (US); Jiangtao Hu, Alameda, CA (US); Chandra Saravanan, Fremont, CA (US)

(73) Assignee: Nanometrics Incorporated, Milpitas, CA (US)

( * ) Notice: Subject to any disclaimer, the term of this patent is extended or adjusted under 35 U.S.C. 154(b) by 421 days.

(21) Appl. No.: 10/937,248

(22) Filed: Sep. 8, 2004

(51) Int. Cl.
*G01B 11/02* (2006.01)
(52) U.S. Cl. .................................................... 356/504
(58) Field of Classification Search ................ 356/451, 356/503, 504, 630, 632, 73; 438/14, 16
See application file for complete search history.

(56) References Cited

U.S. PATENT DOCUMENTS

| | | | |
|---|---|---|---|
| 6,020,968 A * | 2/2000 | Horie | 356/632 |
| 6,166,801 A | 12/2000 | Dishon et al. | 355/27 |
| 6,292,265 B1 | 9/2001 | Finarov et al. | 356/630 |
| 6,368,181 B1 | 4/2002 | Dvir et al. | 451/6 |
| 6,510,395 B2 | 1/2003 | Stanke | 702/81 |
| 6,882,416 B1 * | 4/2005 | Hunter et al. | 356/237.4 |
| 2003/0030822 A1 | 2/2003 | Finarov | 356/636 |
| 2003/0086097 A1 | 5/2003 | Finarov | 356/630 |
| 2004/0106217 A1 | 6/2004 | Higgs | 438/5 |

FOREIGN PATENT DOCUMENTS

| | | |
|---|---|---|
| WO | WO 00/54325 | 9/2000 |
| WO | WO 02/35217 | 5/2002 |
| WO | WO 03/049150 | 6/2003 |

OTHER PUBLICATIONS

Brian E. Stine, et al., "Rapid Characterization and Modeling of Pattern-Dependent Variation in Chemical-Mechanical Polishing" IEEE Transactions on Semiconductor Manufacturing, vol. 11, No. 1, pp. 129-140, Feb. 1998.

* cited by examiner

*Primary Examiner*—Tarifur Chowdhury
*Assistant Examiner*—Jonathon D Cook
(74) *Attorney, Agent, or Firm*—Silicon Valley Patent Group LLP (57) ABSTRACT

A residue detection system collects at least one of the spectrum and image from a measurement region on a sample. Spectral analysis is performed on the collected spectrum to determine whether residue is present and if so the thickness of the residue. The spectral analysis uses a calibration metric that correlates a monitoring parameter to the thickness of the residue. The monitoring parameter is at least one of the reflectance value at one or more of the local minima and maxima in the spectrum, the shape of one or more of the local minima and maxima in the spectrum, and the difference in reflectance values between at least two of the local minima and maxima in the spectrum. In one embodiment, imaging analysis is performed on the collected image of the measurement region if no residue is detected by the spectral analysis.

41 Claims, 7 Drawing Sheets

**Fig. 1A
(Conventional)**

**Fig. 1B
(Conventional)**

**Fig. 2A
(Conventional)**

**Fig. 2B
(Conventional)**

CHARACTERIZING RESIDUE ON A SAMPLE

FIELD OF THE INVENTION

The present invention relates to residue detection and, in particular, to characterizing the residue on a substrate.

BACKGROUND

The use of copper interconnects has been widely adopted by many semiconductor fabrication facilities to meet ever increasing demands for higher capacity and faster processing speed in devices for consumer products. One of the key processes used to form copper interconnects is chemical-mechanical planarization (CMP). CMP is used to remove and planarize layers of deposited materials, such as dielectric and metal materials.

Premature stoppage of the CMP process can result in residue on the wafer scale, i.e., a layer of metal remains over the entire wafer. For example, if the CMP process is stopped too early, a portion of the copper layer may remain along with any underlying barrier layer. Typically, in copper processing, a tantalum (Ta) or tantalum nitride (TaN) layer is used as a barrier metal. Even if residue on the wafer scale is removed, residue on the local scale may remain as a result of topographical variations in the sample. Topographical variations, such as dishing and erosion, are commonly caused by differing polishing rates of different materials and structures on the substrate.

Figure 1A:
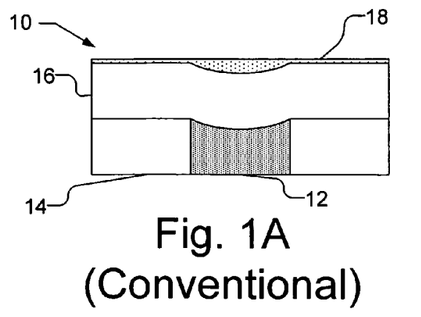
FIGS. 1A and 1B illustrate cross-sectional views of a sample that respectively exhibits wafer scale residue and localized residue as a result of dishing.
Figure 1B:
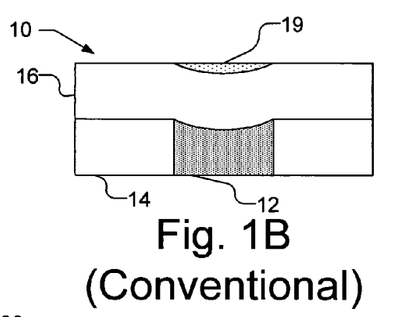

FIGS. 1A and 1B, by way of example, illustrate cross-sectional views of a portion of a sample 10 with wafer scale and localized residue, respectively. Sample 10 includes a first metal 12, e.g., copper, within a dielectric 14. The first metal 12 exhibits dishing. The interlayer dielectric 16 conforms to the surface of the metal 12 and dielectric 14. FIG. 1A illustrates a wafer scale residue that results when a second metal 18 is deposited over the interlayer dielectric 16 and is not completely polished back to the interlayer dielectric 16. FIG. 1B illustrates a localized residue 19 that occurs as a result of dishing in the first metal 12 even when the second metal is completely polished back to the interlayer dielectric 16.

Figures 2A, 2B:
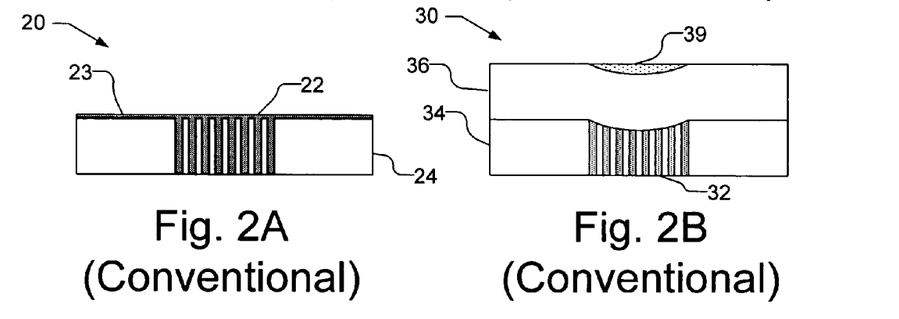
FIGS. 2A and 2B illustrates cross-sectional views of samples that respectively exhibit a wafer scale residue and a localized residue that results from erosion.

FIG. 2A illustrates a cross-sectional view of a portion of a sample 20 with global residue of a metal 22, e.g., copper, over a sample 20 that includes lines, which are formed from a dielectric 24. A barrier metal 23, e.g., of Ta/TaN is shown in FIG. 2A.

FIG. 2B illustrates a cross-sectional view of a portion of a sample 30 with residue that occurs as a result of erosion. Sample 30 includes metal lines 32, which are, e.g., copper and a dielectric 34. The metal lines 32 exhibit erosion. The interlayer dielectric 36 conforms to the surface of the metal lines 32 and when a second metal is polished back to the interlayer dielectric 36, a localized residue 39 remains at the erosion site. Of course, a wafer scale residue may result in FIG. 2B if the second metal is not polished back to the interlayer dielectric 36.

Residual metals, whether on the wafer scale or local scale, can induce device malfunction and breakdown. Therefore, there is an increasing need to control and monitor residue to enhance process yield.

SUMMARY

In accordance with an embodiment of the present invention, a residue detection system collects at least one of the spectrum and image from a measurement region on a sample. Spectral analysis is performed on the collected spectrum to determine whether residue is present and if so the thickness of the residue. The spectral analysis uses a calibration metric that correlates a monitoring parameter to the thickness of the residue. The monitoring parameter is at least one of the reflectance value at one or more of the local minima and maxima in the spectrum, the shape of one or more of the local minima and maxima in the spectrum, and the difference in reflectance values between at least two of the local minima and maxima in the spectrum. In one embodiment, imaging analysis is performed on the collected image of the measurement region if no residue is detected by the spectral analysis. The imaging analysis may include an intensity distribution analysis and an image subtraction analysis.

In one aspect of the present invention, a method of characterizing residue on a sample includes collecting the reflectance spectrum and image for a measurement region on a sample. Spectral analysis on the reflectance spectrum collected from the measurement region is performed. The spectral analysis uses a calibration metric that correlates a monitoring parameter to a thickness of residue. The spectral analysis comprises measuring a monitoring parameter for the collected reflectance spectrum and using the measured monitoring parameter with the calibration metric to determine the thickness of the residue on a measurement region. The method further includes performing at least one of an intensity distribution analysis and image subtraction analysis on the image collected from the measurement region.

In another aspect, a method of characterizing residue on a sample includes collecting the reflectance spectrum and image for a measurement region on a sample at the same time and performing spectral analysis. The spectral analysis includes analyzing at least two of the reflectance value at one or more of the local minima and maxima of the reflectance spectrum, the shape of one or more of the local minima and maxima of the reflectance spectrum, and the difference in reflectance values between at least two of the local minima and maxima of the reflectance spectrum. When the spectral analysis does not indicate that residue is present, an image analysis of the image collected from the measurement region is performed.

In another aspect, an apparatus includes a broadband light source and a beam splitter that directs light produced by the broadband light source towards a sample. An objective lens positioned above the sample focuses light directed by the beam splitter on the sample. The reflected light from the sample is transmitted back through the objective lens. A camera is coupled to receive at least a portion of the reflected light from the sample and a spectrometer is coupled to receive at least a portion of the reflected light from the sample. A computer system is coupled to receive image data from the camera and to receive spectra data from the spectrometer. The computer system includes a computer-usable medium that has a computer-readable program code embodied therein for performing spectral analysis on the spectra data collected from the sample. The code is also for performing an intensity distribution analysis on the image data collected from the sample when the spectral analysis does not indicate that residue is present; and performing an image subtraction analysis on the image data collected from the sample when the intensity distribution analysis does not indicate that residue is present.

In yet another aspect of the present invention, a method of measuring the thickness of residue on a sample includes illuminating a measurement region on the sample with broadband radiation and detecting the reflected spectrum from the sample. The reflected spectrum is analyzed by providing a calibration metric that correlates a monitoring parameter to the thickness of the residue. The monitoring parameter is one of the reflectance value at one or more of the local minima and maxima in the spectrum, the shape of one or more of the local minima and maxima in the spectrum, and the difference in reflectance values between at least two of the local minima and maxima in the spectrum. The monitoring parameter for the detected reflected spectrum is measured and used with the calibration metric to determine the thickness of the residue at the measurement region.

DETAILED DESCRIPTION

Figure 3:
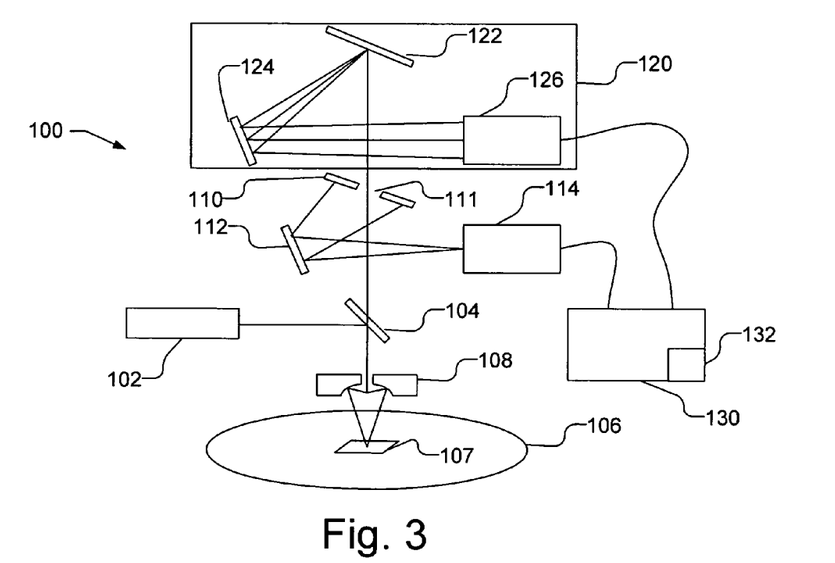
FIG. 3 illustrates a metrology device that may be used in accordance with an embodiment of the present invention.

The residue status of a sample can be quickly and accurately measured using a combined spectral analysis and imaging analysis, in accordance with the present invention. The spectral analysis can be used to not only determine if residue is present, but to determine the amount of residue that is present. Imaging analysis is used to detect the presence of residue that is not detected by spectral analysis. Advantageously, the present invention uses a non-contact system that provides faster metrology feedback, simplified CMP module logistics, and increased overall module productivity. This approach is well suited for any stand-alone, in-line or in-situ copper CMP process monitoring, advanced process control (APC), and on-board applications. Moreover, this approach is not just limited to copper process or any such related process, but extendable to other polishing processes FIG. 3 illustrates a metrology device 100 that may be used in accordance with an embodiment of the present invention to accurately characterize residual material on a substrate using combined spectral and imaging analysis. Metrology device 100 is capable of collecting both spectral data, e.g., using a broadband spectroscopic reflectometer, as well as high resolution image data, e.g., using a CCD camera. By way of example, a NanoOCD/DUV 9010, NanoSpec 9000, 9000i, or 9000b, which may be purchased from Nanometrics Incorporated of Milpitas California, may be used as metrology device 100. Of course, other metrology instruments may be used as metrology device.

As illustrated in FIG. 3, device 100 includes a broadband light source 102, such as a halogen lamp that produces light with a wavelength range of approximately 375 nm to 800 nm. Of course, other light sources and/or wavelengths may be used if desired. A beam splitter 104 directs a portion of the light from light source 102 towards a substrate 106. A lens 108 (or series of lenses), which may has, e.g., 4× or 15× magnification, focuses the light on a test region 107 on the substrate 106 at approximately normal incidence. Light reflected from the test region 107 is collected by lens 108 and a portion of the reflected light passes through the beam splitter 104.

A portion of the reflected light is then reflected by mirrors 110 and 112 to a CCD camera 114 or other appropriate imaging device. The camera 114 images the test region 107, e.g., either in gray-scale or color, or both. The camera may be, e.g., an 8 bit or higher digital camera with an image resolution of up to 1-2 μm/pixel. A cooling system may be used with the camera to minimize the noise level, as well as an adjustable gain for optimizing the image dynamic range.

Another portion of the reflected light passes through an aperture 111 in the mirror 110 and is received by spectrometer 120. As illustrated in FIG. 3, spectrometer 120 includes a grating 122, a mirror 124 and a detector 126, such as a CCD array. The grating diffracts the reflected light into its constituent wavelengths, which are reflected by mirror 124 to the detector 126. The detector 126 collects the reflected light as a function of wavelength.

While FIG. 3 shows a spectroscopic reflectometer, it should be understood that other metrology devices may alternatively be used, such as an ellipsometer or scatterometer.

The device 100 includes a processor 130 that is coupled to receive the data from the camera 114 and the spectrometer 120. The same processor 130 or a different processor may be used to control the operation of the device 100. The processor 130 may be, e.g., a workstation, a personal computer, or central processing unit, e.g., Pentium 4™ or other adequate computer system. Processor 130 includes a computer-usable medium 132, which may be, e.g., RAM, a hard drive, or both, and which is used to record the data provided by the camera 114 and spectrometer 120 as well as the results of the analysis performed by processor 130. The processor 130 also includes other conventional systems such as a user interface and monitor or printer. The processor 130 includes a computer-readable program code embodied, e.g., on the medium 132, which is for analyzing the residue on a substrate, in accordance with the present invention. Generating code to analyze the residue on a substrate is well within the abilities of those skilled in the art in light of the present disclosure.

In operation, the device 100 produces image data and spectral data from the measurement region 107, which are analyzed to provide an accurate analysis of any residue, including the amount of residue on the test sample. Prior art devices, on the other hand, do not provide an accurate quantitative analysis of the residue. Without an accurate quantitative analysis in which the precise thickness of the residue is determined, the measurement is inappropriate for process control.

Figure 4:
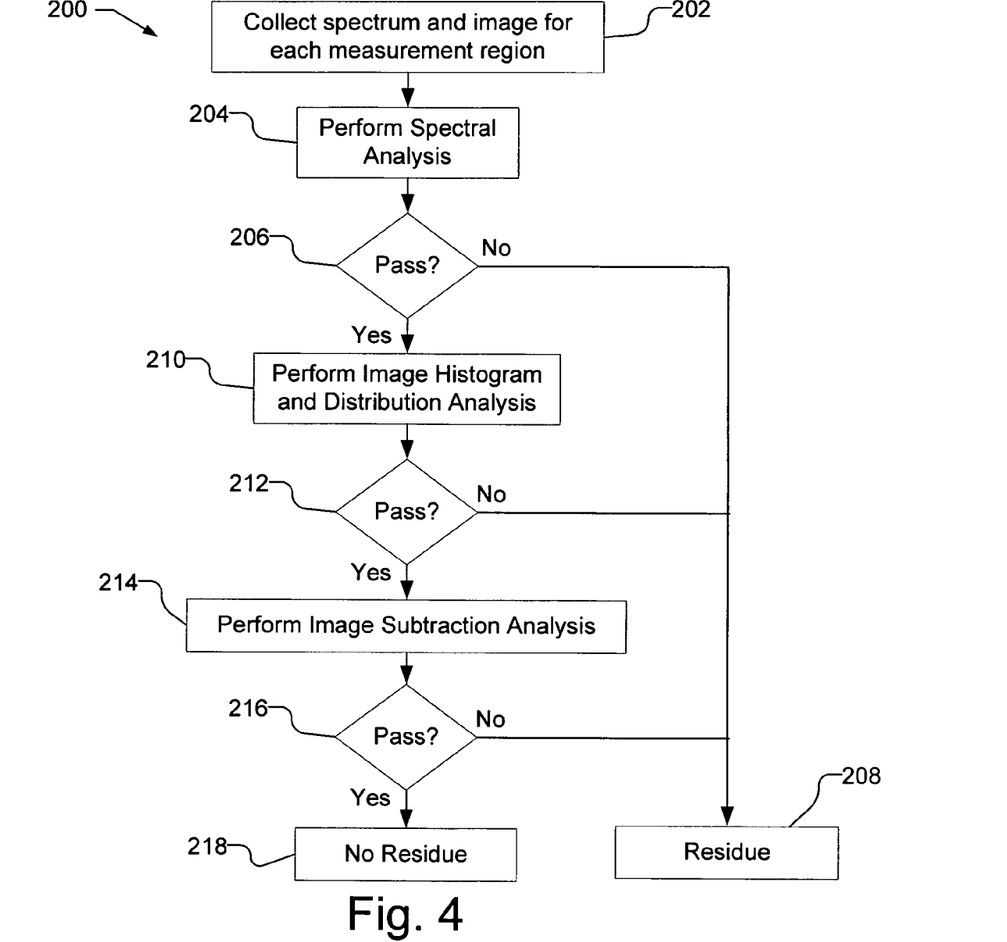
FIG. 4 shows a flow chart of the process of determining the presence of residue in accordance with an embodiment of the present invention.

FIG. 4 shows a flow chart 200 of the process of determining the presence of residue in accordance with an embodiment of the present invention. As illustrated in FIG. 4, the spectrum and image for the measurement region is collected (step 202). If desired, the spectrum and image data for a plurality of measurement regions on the sample may be collected before analyzing the data. Alternatively, the spectrum and image data from each measurement region may be analyzed prior to collecting the spectrum and image data for the next measurement region. The spectrum and image of the measurement region may be collected by, e.g., device 100 shown in FIG. 3, or if desired, other devices may be used including separate spectral and imaging systems.

A spectral analysis of the measurement region is then performed (step 204). The spectral analysis is based on the fact that properties of residues (residue type and thickness) significantly change the reflectance spectrum. Spectral analysis is described in more detail below in reference to FIGS. 6-10. If the spectral analysis determines that residue is present on the measurement region (step 206), the substrate does not pass (step 208). Anytime the sample does not pass (step 208) appropriate action may be taken, e.g., the device 100 may indicate that residue is present and the sample is reprocessed or rejected. If, on the other hand, the spectral analysis does not indicate that residue is present (step 206), further analysis in the form of image analysis may be performed.

The image analysis includes an intensity distribution analysis of the measurement region (step 210) that uses the image collected in step 202. Distribution analysis is described in more detail below in reference to FIGS. 11-13. If the distribution analysis determines that residue is present on the measurement region (step 212), the substrate does not pass (step 208). If, on the other hand, the distribution analysis does not indicate that residue is present (step 212), image subtraction analysis is performed.

Image subtraction analysis may be performed on the measurement region using the same image collected by the device 100 (step 214). Subtraction analysis is described in more detail below in reference to FIGS. 14-15. If the measurement region does not pass (step 216) the image subtraction analysis, residue is present on the substrate (step 208). On the other hand, if the substrate passes the image subtraction analysis, the measurement region is considered to be free from residue (step 218).

It should be understood that if desired, the order of the spectral analysis and the imaging analysis may be reversed. For example, it may be advantageous to perform the imaging analysis in order to locate the position of any residue prior to collecting the spectrum and performing the spectral analysis.

Spectral Analysis

Figure 5:
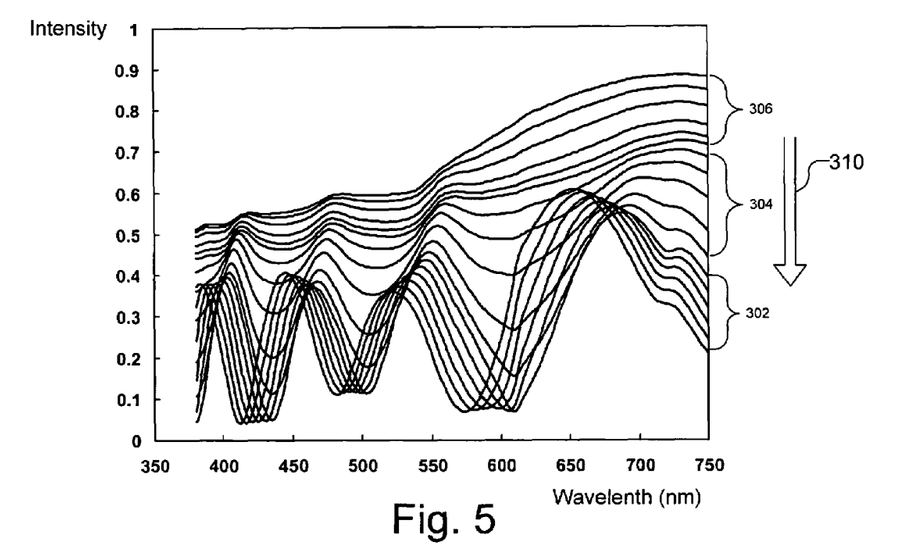
FIG. 5 illustrates several simulated spectra from a measurement region that includes a metal/dielectric grating over interlayer dielectrics.
Figure 6:
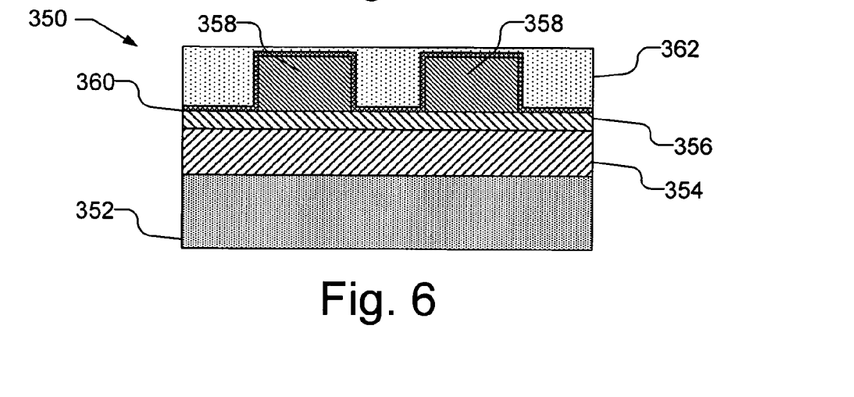
FIG. 6 illustrates a cross section of an exemplary model structure that may produce the spectra shown in FIG. 5 as the thicknesses of various layers are altered.

The spectral analysis from step 204 in FIG. 4 is based on the fact that properties of residues (residue type and thickness) significantly change the reflectance spectrum. By way of example, FIG. 5 illustrates several simulated spectra from a measurement region that includes a metal/dielectric grating over interlayer dielectrics. FIG. 6 illustrates a cross section of an exemplary model structure 350 that may produce spectra such as that shown in FIG. 5 as the thicknesses of various layers are altered. The model structure 350 includes a silicon substrate 352 that is covered with a layer 354 that is, e.g., 300 nm of $SiO_2$, and a layer 356 that is, e.g., 100 nm of $Si_3N_4$. Grating structures 358 overlay layer 356 and are, e.g., $SiO_2$ that is 500 nm thick with line widths of 0.5 µm. A barrier layer 360 covers the grating structures 358 and exposed portions of layer 356. The barrier layer 360 may be, e.g., 25 nm of Ta/TaN. A copper layer 362 overlies the barrier layer 360.

The spectra shown in FIG. 5 illustrate the simulated spectra from model structure 350 as the copper layer 362 and barrier layer 360 are polished back. For example, the spectra labeled 306 in FIG. 5 are produced as a result of the copper layer 362 being present on the model structure 350. As the thickness of the copper layer 362 is reduced, e.g., from polishing, the intensity of the spectra is generally reduced, as indicated by arrow 310.

The spectra 304 are produced by the model structure 350 once the copper layer 362 is polished back to the barrier layer 360. As the thickness of the barrier layer 360 is reduced, the intensity of the spectra is generally reduced.

The spectra 302 in FIG. 5 are produced by the model structure 350 after the barrier layer 360 is polished back to the $SiO_2$ grating structure 358, i.e., there is no residue left on the model structure. With continued polishing of the model structure, i.e., the thickness of the grating structure 358 is reduced, a complicated set of spectra 302 is produced. As can be seen in FIG. 5, however, the spectra 302 include local minimas, sometimes referred to as valleys, which have approximately the same intensity and a wavelength shift. Thus, continued polishing of the model structure 350 once the residue is removed results in specta with valleys with approximately the same intensity.

As can be seen in FIG. 5, as the thicknesses of the different layers change, the spectra manifests changes in the peak and valley regions. The changes in the spectra may be measured in various manners, such as the difference in intensity values at the peaks and/or valleys of the spectra, the shape of the spectra near a peak and/or valley, and the peak to valley difference in the spectra. If more than one valley or peak is selected for monitoring, the averaged value may be used as the monitoring parameter. Any or all of the changes manifested in the spectra may be measured during the spectral analysis.

To measure the reflectance spectrum from a sample, selected peaks or valleys are traced by finding local minimums (for valleys) or maximums (for peaks) in pre-defined regions in the spectrum. If the peak or valley reflectance is used as the monitoring parameter, the peaks/valleys are related to both the residue properties as well as functions of the underlying film structure, especially the dielectric thickness, as illustrated by spectra 302. However, as shown in FIG. 5, the process variations in dielectric layer thickness mainly cause a wavelength shift of the peak and valley positions, whereas variations in residue thickness will alter the reflectance. Accordingly, by tracing of the peaks or valleys of the spectra, these effects caused by underlying dielectric thickness variations and residue thickness variations are decoupled, giving a true relationship between the peak/valley reflectance and the residue thickness.

Figure 7:
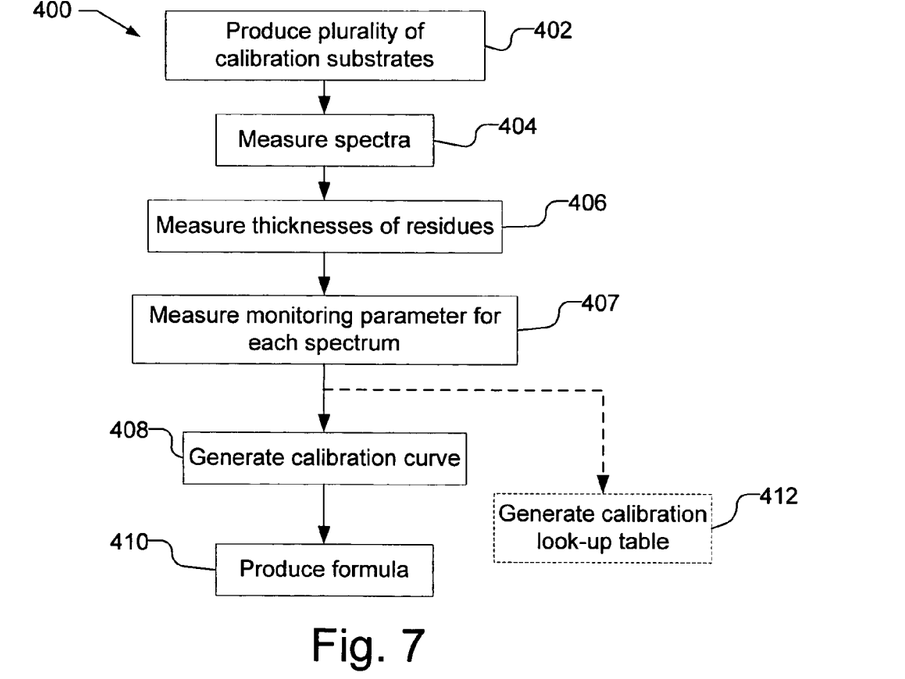
FIG. 7 is a flow chart illustrating a method of calibrating the spectral analysis.

To perform the spectral analysis, a calibration metric that correlates a monitoring parameter to the thickness of the residue is provided. FIG. 7 is a flow chart illustrating a method of generating a calibration metric. As illustrated in FIG. 7, a number of calibration substrates are produced (step 402). Each calibration substrate includes the same underlying structure as the structure that is to be measured. However, the calibration substrates also include differing thicknesses of residue over the structures, which include the normal process variations. By way of example, the calibration substrates may be produced in the same manner as the device that is to be measured. The differing thicknesses of residue may be produced by CMP polishing each substrate for a different amount of time.

The spectra for the different calibration substrates are then measured (step 404). Because the calibration substrates have differing amounts of residue, the resulting spectra will be similar to that shown in FIG. 5. Once the spectra is measured for the calibration substrates, the actual thicknesses of the residues on the calibration substrates are measured, e.g., using a scanning electron microscope or other appropriate techniques (step 406). A destructive measurement technique may be used to determine the actual thickness of the residue.

With the spectra measured and the actual thickness of the residue measured, the monitoring parameter for each spectrum is measured (step 407). A calibration curve can be generated for the monitoring parameter (step 408), e.g., reflectance values, spectra shape, or peak to valley difference. The calibration curve may be produced using one or more valleys/peaks of the measured spectra. If more than one valley or peak is selected, the averaged value may be used as the monitoring parameter.

Based on the calibration curve, a semi-empirical equation can then be generated to fit the calibration curve and that can be used to determine the thickness of residue on a test sample based on the measured spectra (step 410). It should be understood, of course, that the calibration curve and the resulting equation may be produced at the same time and, in fact, the calibration curve need not be physically produced. As illustrated in FIG. 7, in another embodiment, a calibration look-up table is produced (step 412) instead of a calibration curve and the semi-empirical equation.

In practice, once the equation or look-up table is produced, the spectral analysis of a test sample is performed by measuring the spectrum of the test sample and inputting the monitoring parameter from the test spectra into the calibration equation or look-up table. Of course, the same monitoring parameter, e.g., peak and/or valley, are used in the spectral analysis of the test sample as used to generate the calibration data.

Figure 8:
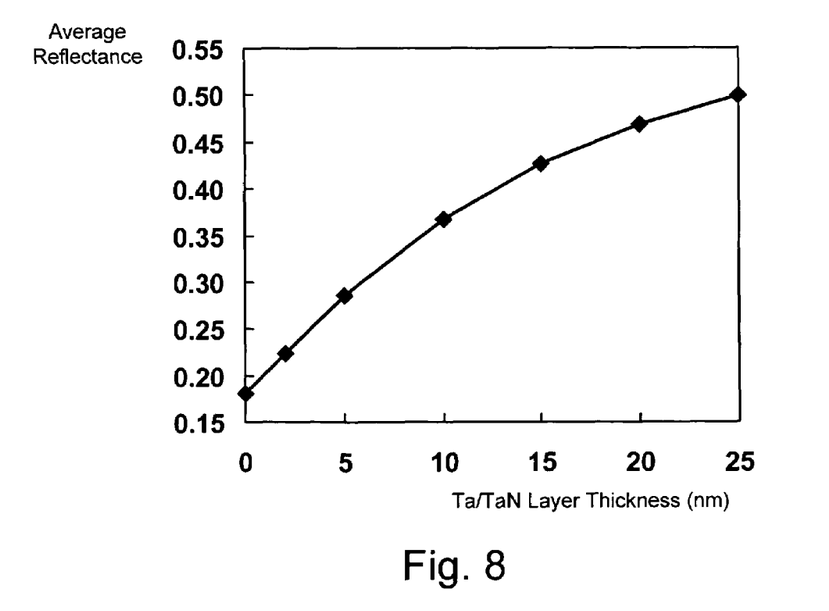
FIG. 8 shows relationship between the valley reflectance value and the residue thickness for spectra in FIG. 5.

The reflectance values at one or more peak and/or valley can be used as the monitoring parameter. FIG. 8 shows the reflectance value versus residue thickness based on the spectra 304 from FIG. 5. As can be seen in FIG. 8, there is an increased reflectance for thicker residues.

The calibration curve illustrated in FIG. 8 can be quantified using a semi-empirical equation that approximately describes the curve. By way of example, one semi-empirical equation that may be used is the exponential type as follows:

$$R = R_0 + (R_m - R_0)(1 - \exp(-kl)) \qquad \text{eq. 1}$$

where $R_0$ and $R_m$ are the reflectance values at the valley position of the spectra corresponding to no residue and a very thick Ta/TaN residue (an opaque layer) respectively, k is the absorption coefficient of the metal and l is the residue thickness.

Alternatively, a polynomial may be used to describe the curve as follows:

$$R = \sum_{n=0}^{m} A_n l^n \qquad \text{eq. 2}$$

where $A_n$ is the coefficient of the $n^{th}$ polynomial term and l is the residue thickness. If desired, other equations may be used to describe the curve. Moreover, different equations may be used for different residue types. Further, different equations may be used to describe the curve at different thickness regions.

Once the calibration metric is produced, e.g., by fitting the curve shown in FIG. 8 to an equation, the presence and thickness of residue on a test sample can be determined by collecting the spectrum from the target and measuring the desired monitoring parameter, i.e., the measured reflectance at a designated peak and/or valley and using the monitoring parameter with the calibration equation to determine the thickness of the reside. Alternatively, the calibration metric may be a lookup table, where the monitoring parameter is used with the look-up table to determine the residue thickness and where a piece-wise interpolation may be used if the value of the monitoring parameter for the collected spectrum is between data points on the look-up table.

In some structures, when residues are thin, e.g., less than approximately 20 Å for Ta/TaN, the reflectance value may produce a non-unique thickness. Accordingly, the reflectance values cannot be used to provide an accurate measurement of very thin residues.

Figure 9:
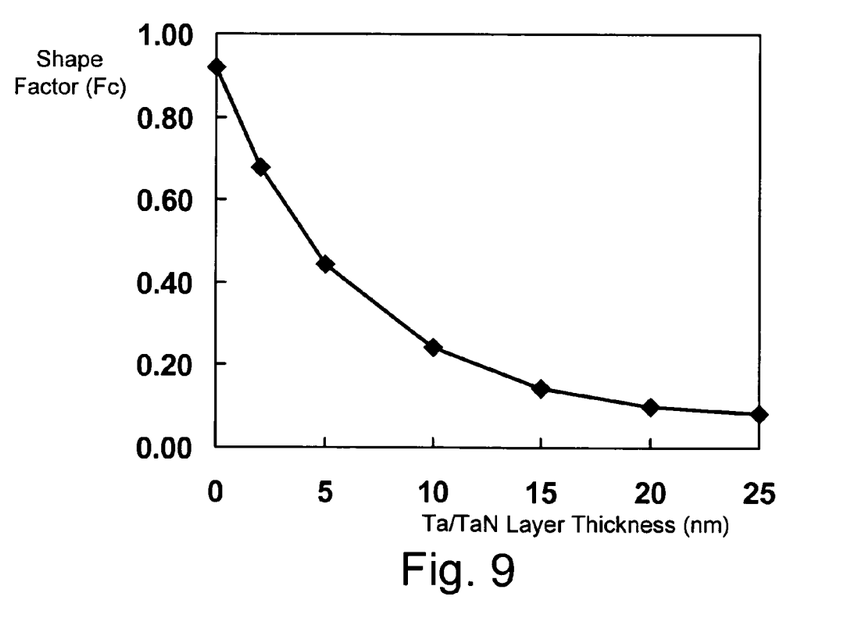
FIG. 9 shows the relationship between the shape factor near a valley and the residue thickness for spectra in FIG. 5.

Due to the non-unique result of the reflectance values for very thin residues, it may be desirable to perform additional spectral analysis to more accurately measure the thickness of the residue. A second monitoring parameter that can be used for residue thickness measurement is the shape of the spectra at a peak or valley region. The shape factor may be defined as:

$$F_c = \sum_{i=n}^{m} \left| \frac{R_i - R_{i-1}}{\lambda_i - \lambda_{i-1}} \right| \qquad \text{eq. 3}$$

where n and m represent the $n^{th}$ and $m^{th}$ data points near a peak or a valley region, and $R_i$ and $\lambda_i$ are the respective reflectance and wavelength of the $i^{th}$ data point. FIG. 9 is a graph showing the relationship between the shape factor near a valley (approximately at 525 nm) and the Ta/TaN residue thickness for the spectra 304 in FIG. 5. As can be seen in FIG. 9, the shape factor is smaller for increased Ta/TaN residue thicknesses.

As described above (step 410 in FIG. 7), a semi-empirical equation can be produced that describes the curve shown in FIG. 9. The equation may be, e.g., exponential or polynomial. Alternatively, a look-up table for the residue measurement based on shape factor may be produced.

The shape factor for a peak and/or valley of the spectra from the test sample can be derived using equation 3. The derived shape factor for the test sample can then be input into the equation or look-up table to derive the thickness of the residue.

Figure 10:
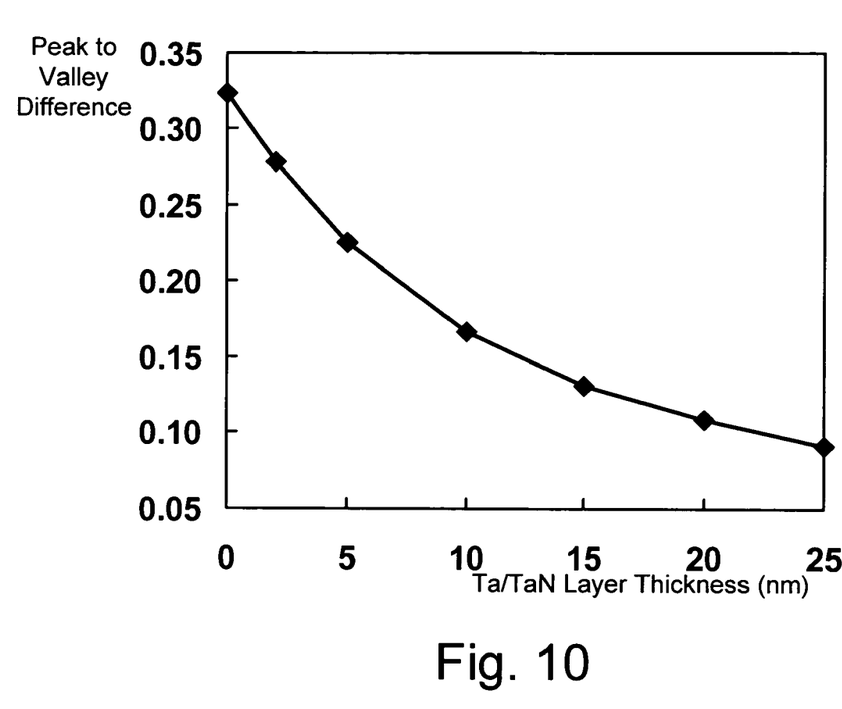
FIG. 10 shows the relationship between the difference in reflectance values of the local maxima and/or minima and the residue thickness for spectra in FIG. 5.

The third parameter that can be used for residue thickness measurement is the difference in reflectance values between the local maximum and/or minimum, such as peak to valley difference. If desired, peak to peak or valley to valley may alternatively be used. FIG. 10 illustrates the dependence of this parameter against the Ta/TaN residue thickness for the spectra 304 in FIG. 5. The peak to valley difference reflects the oscillating nature of the dielectric reflectance spectrum. When the residue thickness increases, this oscillation normally becomes weaker and finally vanishes. This trend can be used for residue measurement using the same methodology discussed above by creating an equation that describes the calibration curve or a look-up table and using the difference between the local maxima and minima in the spectra from the test sample with the derived equation or look-up table to determine the thickness of the residue.

In one embodiment, two or more of the parameters are used together in the spectral analysis. The results provided by each of the parameters may be averaged or otherwise combined. The use of multiple parameters together, advantageously provides a higher success rate of accurately measuring the thickness of the residue than is found in prior art methods.

It should be understood that the spectral analysis may be performed using forms other than the original spectra, such as differential or Fourier transforms of the original spectra.

As discussed in FIG. 4, if the measurement region of the sample does not pass the spectral analysis, it is known that residue is present on the test sample. The spectral analysis can advantageously provide an accurate measurement of the residue thickness. If, on the other hand, the measurement region of the sample passes the spectral analysis, residue may still be present, but in insufficient quantities to be detected by the spectral analysis. For example, the spectral analysis may be performed on an area that is smaller than the imaged area. If the residue resides outside the measurement area, spectral analysis may simply miss the residue that is present on the sample. Accordingly, imaging analysis is performed to ensure that local scale residue is not overlooked.

Imaging Analysis

The presence of metal residues on the sample surface can be detected using imaging analysis, which, as discussed in FIG. 4, includes intensity distribution analysis (step 210) and subtraction analysis (214). The residue imaging analysis may be performed using the digital images recorded at step 202 in FIG. 3, e.g., using the CCD camera 114 shown in FIG. 3.

Figure 11:
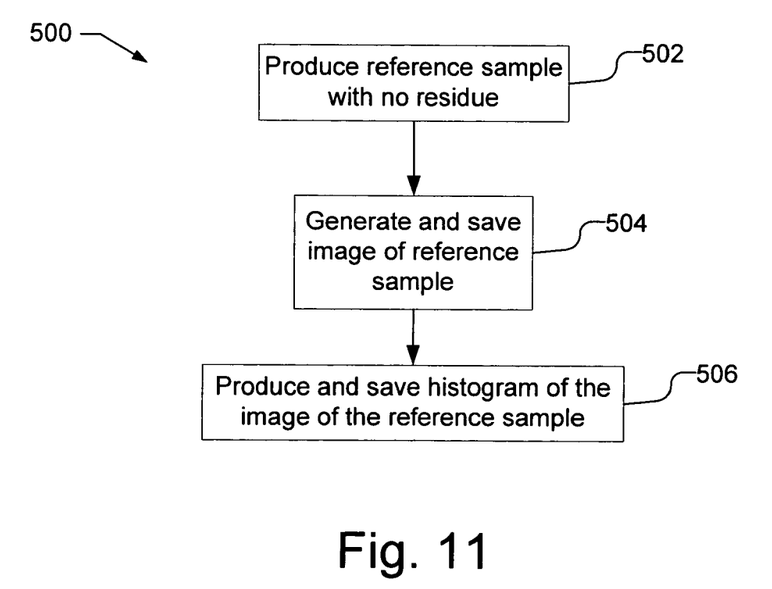
FIG. 11 is a flow chart of a process of producing a reference histogram.
Figure 12A:
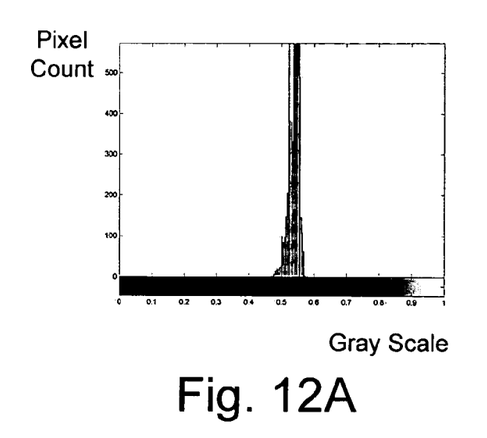
FIGS. 12A and 12B illustrate a histogram of a reference sample and a test sample, respectively.

The intensity distribution analysis uses histograms to analyze the distribution of the image intensity of the test sample. To perform the distribution analysis, a reference histogram is produced. FIG. 11 is a flow chart 500 of a process of producing a reference histogram. First, a reference sample that has no residue is produced (step 502). If desired, the reference sample may be a calibration substrate with no residue produced in step 402 of FIG. 7. An image of the reference sample is then generated (step 504) using the device that will be used to produce the image of the test sample to ensure that the quality of the images are the same. A histogram of the image of the reference sample is then produced and saved (step 506). The histogram may be produced, e.g., by binning the intensities from a gray scale image produced by an 8-bit or 12-bit camera. FIG. 12A illustrates a histogram of a reference sample.

Figure 12B:
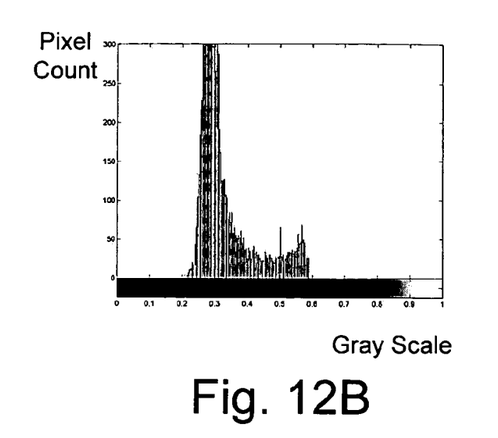
Figure 13:
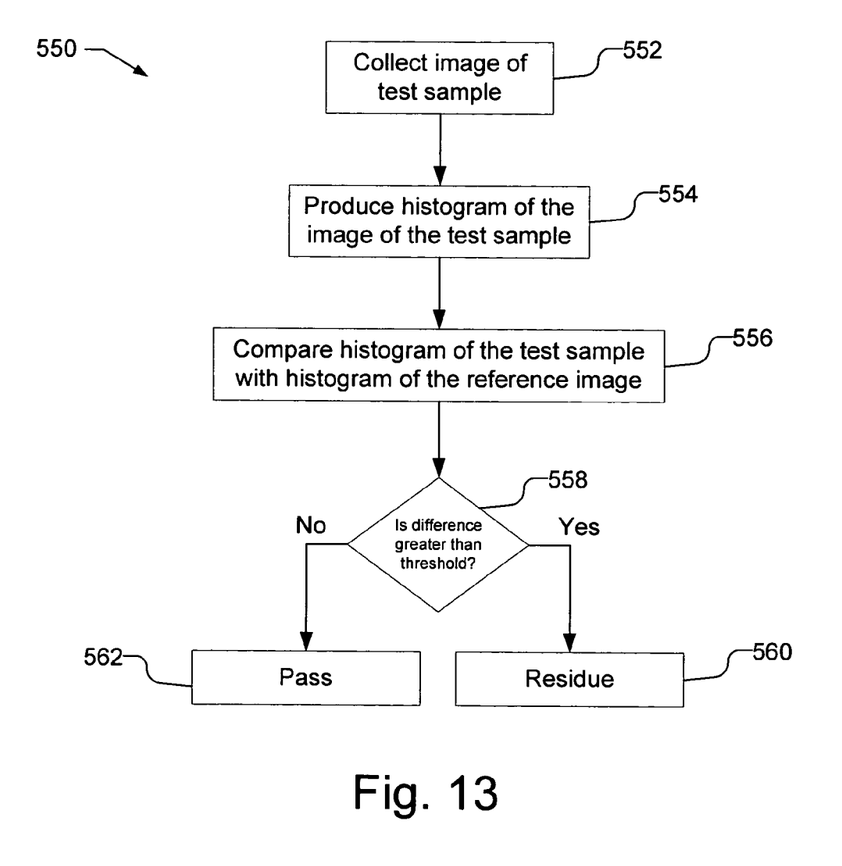
FIG. 13 is a flow chart illustrating the process of analyzing the intensity distribution of the image from the sample under test.

FIG. 13 is a flow chart 550 illustrating the process of analyzing the intensity distribution of the image from the sample under test. The image of the test sample is collected (step 552). The collection of the image of the test sample is described, e.g., in reference to step 202 in FIG. 4. The histogram of the image of the test sample is then produced (step 554) in the same manner that the histogram of the image of the reference sample is produced. FIG. 12B illustrates a histogram from a test sample. As can be seen in FIGS. 12A and 12B, the clean reference image has much narrower pixel intensity distribution than the image of the test sample that has residue.

The histogram from the test sample is compared to the histogram of the reference image (step 556). The histograms may be compared, e.g., by comparing the standard deviation (real or integer multiples of the standard deviation) of the intensity distributions. The presence of residue can be determined based on a threshold difference in the standard deviations. Other metrics may also be used, e.g., by fitting the histograms to probability distributions and calculating the difference in higher order moments, and calculating differences in projections of measured histograms and probability distributions. As illustrated in FIG. 13, if the difference in the histogram of the reference image and the test image is greater than or equal to a pre-set threshold (step 558), the test sample is considered to have residue and therefore fails (step 560). If the difference is less than the threshold, the test sample is considered to have no or an insignificant amount of residue, and therefore passes (step 562).

Figure 14:
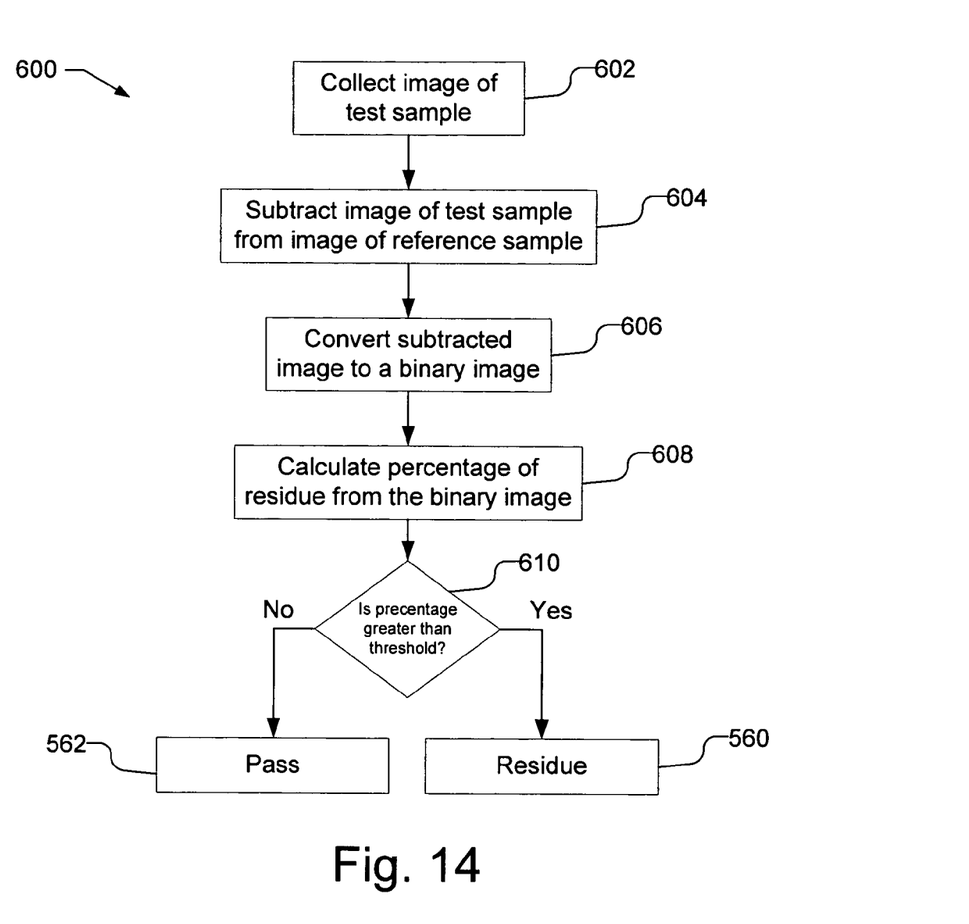
FIG. 14 is a flow chart of the process of performing subtraction analysis.
Figure 15:
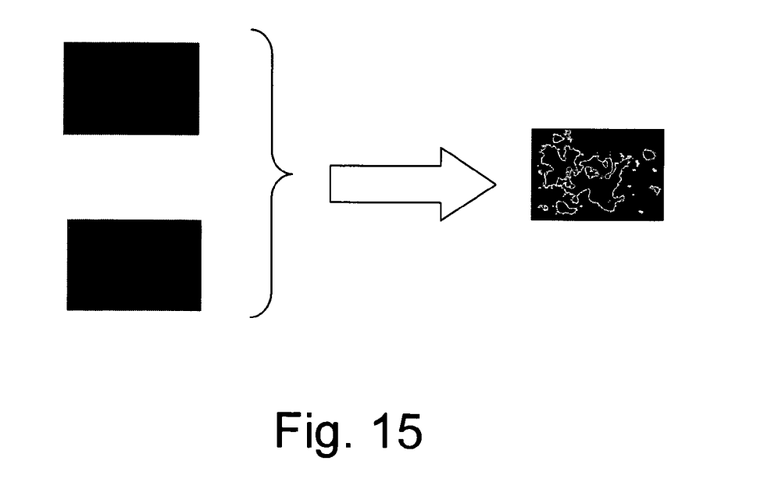
FIG. 15 illustrates an image of a test sample, a reference sample, and an image formed by subtracting the test image from the reference image.

If the test sample passes the intensity distribution analysis, a small amount of residue may still be present on the test sample. Accordingly, an additional imaging analysis, in the form of subtraction analysis, is performed. FIG. 14 is a flow chart 600 of the process of performing subtraction analysis. The image of the test sample is collected in step 602. The image of the test sample collected during the intensity distribution analysis, e.g., at step 552 in FIG. 13 may be used. FIG. 15 illustrates an image 652 of a test sample. The subtraction analysis uses an image of a clean reference sample, such as that generated and stored at step 504 in FIG. 11. FIG. 15 illustrates an image 654 of the reference sample. The histograms for the test sample and the reference sample may be used to correct for any background differences in the images.

As illustrated in FIG. 14, the image of the test sample is digitally subtracted from the image of the reference sample (step 604) at a pixel to pixel level. Prior to image subtraction, the test sample image should be aligned with the reference image, e.g., by aligning a high-contrast feature in the image (not shown in FIG. 14). The subtracted image is then converted to a binary image (step 606) using a threshold. The threshold value is determined by the image intensity variations for clean samples on different wafers, e.g., wafer to wafer or lot to lot variations.

FIG. 15 illustrates the resulting binary image 656 after subtraction of the test sample 652 from the reference sample 654. The binary image can then be used to calculate the residue percentage, i.e., the amount of residue with respect to the area of the sample (step 608). If the percentage of residue is greater than a threshold (step 610), residue is considered to be present on the test sample (612). If, on the other hand, the percentage is less than the threshold, no residue is considered to be present (step 614). Of course, some residue may still be present, but by setting the threshold to an appropriate level, e.g., one percent, any residue that remains on a test sample that passes will be negligible.

Further analysis can be done by calculating the residue sizes by counting the number of connected pixels in the binary image. Even if the percentage of residue pixels is below the set threshold, residues can still be reported if a threshold number of pixels are connected. By way of example, with a residue threshold of, e.g., one percent out of approximately 1600 pixels, the presence of five connected pixels may still be denoted as residue even though the total number of pixels is less than the threshold percentage.

If the imaging analysis indicates that residue with a size comparable to the measurement spot size for the spectral analysis, is present on the test sample at a specific location, additional spectral analysis, discussed above, may be performed at that specific location to determine the type and thickness of the residue.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of characterizing residue on a sample, the method comprising:
   collecting a reflectance spectrum and image for a measurement region on a sample;
   performing spectral analysis on the reflectance spectrum collected from the measurement region, wherein the spectral analysis uses a calibration metric that correlates a monitoring parameter to a thickness of residue and wherein the spectral analysis comprises measuring a monitoring parameter for the collected reflectance spectrum and using the measured monitoring parameter with the calibration metric to determine the thickness of the residue on a measurement region;
   performing at least one of an intensity distribution analysis and image subtraction analysis on the image collected from the measurement region; and
   recording the results of the characterizing residue on the sample.

2. The method of claim 1, wherein the spectral analysis is performed before performing at least one of an intensity distribution analysis and image subtraction analysis on the image.

3. The method of claim 2, wherein the at least one of an intensity distribution analysis and image subtraction analysis is performed when the spectral analysis does not indicate that residue is present.

4. The method of claim 3, further comprising collecting an additional reflectance spectrum at a different location within the measurement region and performing spectral analysis on the additional reflectance spectrum when the at least one of an intensity distribution analysis and image subtraction analysis indicates that residue is present at the different location within the measurement region.

5. The method of claim 1, wherein the at least one of an intensity distribution analysis and image subtraction analysis on the image is performed before performing the spectral analysis.

6. The method of claim 1, wherein collecting the reflectance spectrum and image for a measurement region on a sample comprises:
   illuminating the measurement region with broadband radiation;
   collecting a portion of the radiation that is reflected by the measurement region with a spectrometer; and
   collecting another portion of the reflected light with a camera.

7. The method of claim 1, wherein the spectral analysis uses a plurality of calibration metrics that correlate a respective plurality of monitoring parameters to the thickness of residue and wherein the spectral analysis comprises measuring a plurality of monitoring parameters for the collected reflectance spectrum and using the plurality of measured monitoring parameter with the plurality of calibration metrics to determine the thickness of the residue on a measurement region.

8. The method of claim 1, wherein the monitoring parameter is at least one of the reflectance value at one or more of the local minima and maxima of the reflectance spectrum, the shape of one or more of the local minima and maxima of the reflectance spectrum, and the difference in reflectance values between at least two of the local minima and maxima of the reflectance spectrum.

9. The method of claim 1, wherein the spectral analysis further comprises generating the calibration metric that correlates a monitoring parameter to the thickness of the residue, generating the calibration metric comprises:
   producing a plurality of calibration substrates, each calibration substrate having a calibration region with the same underlying structure as the measurement region on the sample and a different thickness of residue over the underlying structure;
   collecting the reflectance spectrum for each of the calibration regions;
   measuring the monitoring parameter for each collected reflectance spectrum;
   measuring the thicknesses of the residue on the calibration regions;
   generating the calibration metric by correlating the monitoring parameter for each of the calibration regions to the thickness of the residue on the calibration regions.

10. The method of claim 9, wherein the calibration metric is at least one calibration equation that correlates the monitoring parameter to the thickness of the residue.

11. The method of claim 9, wherein the calibration metric is a calibration look-up table that correlates a number of values for the monitoring parameter to the thickness of the residue.

12. The method of claim 11, wherein interpolation is used to correlate values for the monitoring parameter that fall between the number of values in the calibration look-up table to the thickness of the residue.

13. The method of claim 1, wherein performing an intensity distribution analysis on the image collected from the measurement region comprises:
   producing a reference intensity distribution for a reference sample that has no residue;
   producing an intensity distribution for the image of the measurement region on the sample;
   comparing the intensity distribution for the image to the reference intensity distribution; and
   determining that residue is present on the measurement region when the comparison between the intensity distribution for the image to the reference intensity distribution exceeds a predetermined threshold.

14. The method of claim 1, wherein performing image subtraction analysis on the image collected from the measurement region comprises:
   producing a reference image for a reference sample that has no residue;
   subtracting the image of the measurement region from the reference image;
   converting the subtracted image to a binary image; and
   calculating the percentage of residue from the binary image.

15. The method of claim 1, wherein the calibration metric correlates the monitoring parameter to a quantitative thickness of residue and wherein the quantitative thickness of the residue on a measurement region is determined.

16. The method of claim 1, wherein the residue on the sample is produced by the incomplete removal of at least one of a barrier layer and a top layer that overlies the barrier layer, and wherein using the measured monitoring parameter with the calibration metric to determine the thickness of the residue determines the thickness of the incompletely removed, at least one of the barrier layer and the top layer.

17. A method of characterizing residue on a sample, the method comprising:
   collecting a reflectance spectrum and image for a measurement region on a sample at the same time;
   performing spectral analysis by analyzing at least one of a reflectance value at one or more of a local minima and maxima of the reflectance spectrum, a shape of one or more of the local minima and maxima of the reflectance spectrum, and a difference in reflectance values between at least two of the local minima and maxima of the reflectance spectrum;
   performing an image analysis of the image collected from the measurement region as a result of the spectral analysis indicating that residue is not present; and
   recording the results of the characterizing residue on the sample.

18. The method of claim 17, wherein performing an image analysis comprises:
   performing an image analysis of an intensity distribution analysis on the image collected from the measurement region when the spectral analysis does not indicate that residue is present; and
   performing an image subtraction analysis on the image collected from the measurement region when the intensity distribution analysis does not indicate that residue is present.

19. The method of claim 17, wherein performing spectral analysis comprises analyzing each of the reflectance values at one or more of the local minima and maxima of the reflectance spectrum, the shape of one or more of the local minima and maxima of the reflectance spectrum, and the difference in reflectance values between at least two of the local minima and maxima of the reflectance spectrum.

20. The method of claim 17, further comprising:
   producing a plurality of calibration substrates, each calibration substrate having the same underlying structure as the measurement region, wherein the calibration substrates have different thicknesses of residue over the underlying structure;
   measuring the spectra from the plurality of calibration substrates; and
   measuring the thicknesses of the residues on the plurality of calibration substrates.

21. The method of claim 20, further comprising producing a look-up table that relates the measured spectra from the plurality of calibration substrates to the thicknesses of the residues.

22. The method of claim 20, further comprising:
   generating calibration curves for at least two of the reflectance values at one or more of the local minima and maxima of the measured spectra with respect to thicknesses of the residues, the shape of one or more of the local minima and maxima of measured spectra with respect to the thicknesses of the residues, and the difference in reflectance values between at least two of the local minima and maxima of the measured spectra with respect to the thicknesses of the residues; and
   generating calibration equations that describe the calibration curves, wherein performing spectral analysis includes using the calibration equations.

23. The method of claim 17, wherein performing an image analysis of the image collected from the measurement region comprises:
   producing a reference intensity distribution for a reference sample that has no residue;
      producing an intensity distribution for the image of the measurement region on the sample; and
      comparing the intensity distribution for the image to the reference intensity distribution.

24. The method of claim 17, wherein performing an image analysis of the image collected from the measurement region comprises:
   producing a reference image for a reference sample that has no residue;
   subtracting the image of the measurement region from the reference image;
   converting the subtracted image to a binary image; and
   calculating the percentage of residue from the binary image.

25. An apparatus comprising:
   a broadband light source;
   a beam splitter that directs light produced by the broadband light source towards a sample;
   an objective lens positioned above the sample to focus light directed by the beam splitter on the sample, wherein reflected light from the sample is transmitted back through the objective lens;
   a camera coupled to receive at least a portion of the reflected light from the sample;
   a spectrometer coupled to receive at least a portion of the reflected light from the sample;
   a computer system coupled to receive image data from the camera and to receive spectra data from the spectrometer, the computer system having a computer-usable medium having computer-readable program code embodied therein for:
   performing spectral analysis on the spectra data collected from the sample;
   performing an intensity distribution analysis on the image data collected from the sample when the spectral analysis does not indicate that residue is present; and
   performing an image subtraction analysis on the image data collected from the sample as a result of the intensity distribution analysis indicating that residue is not present.

26. A method of measuring the thickness of residue on a sample, the method comprising:
   illuminating a measurement region on the sample with broadband radiation;
   detecting a reflected spectrum from the sample;
   analyzing the reflected spectrum, wherein analyzing the reflected spectrum comprises:
      providing a calibration metric that correlates a monitoring parameter to the thickness of the residue, wherein the monitoring parameter is one of the reflectance value at one or more of a local minima and maxima in the spectrum, a shape of one or more of the local minima and maxima in the spectrum, and a difference in reflectance values between at least two of the local minima and maxima in the spectrum;
      measuring the monitoring parameter for the detected reflected spectrum, using the measured monitoring parameter and the calibration metric to determine the thickness of the residue at the measurement region; and recording the results of the measuring the thickness of residue.

27. The method of claim 26, wherein analyzing the reflected spectrum comprises:

providing a separate calibration metric for a plurality of monitoring parameters, each calibration metric correlates a monitoring parameter to the thickness of the residue;

measuring the plurality of monitoring parameters for the detected reflected spectrum; and using the measured plurality of monitoring parameters and the calibration metrics to determine the thickness of the residue at the measurement region.

28. The method of claim 26, wherein providing a calibration metric that correlates a monitoring parameter to the thickness of the residue comprises:

producing a plurality of calibration substrates, each calibration substrate having a calibration region with the same underlying structure as the measurement region on the sample and a different thickness of residue over the underlying structure;

illuminating each of the calibration regions;

detecting the reflected spectrum from each of the calibration regions;

measuring the monitoring parameter for each of the detected reflected spectra from the calibration regions;

measuring the thicknesses of the residue on the calibration regions;

generating the calibration metric by correlating the monitoring parameter for each of the calibration regions to the thickness of the residue on the calibration regions.

29. The method of claim 28, wherein the calibration metric is at least one calibration equation that correlates the monitoring parameter to the thickness of the residue.

30. The method of claim 28, wherein the calibration metric is a calibration look-up table that correlates a number of values for the monitoring parameter to the thickness of the residue.

31. The method of claim 30, wherein interpolation is used to correlate values for the monitoring parameter that fall between the number of values in the calibration look-up table to the thickness of the residue.

32. The method of claim 26, further comprising:

collecting an image of the measurement region on the sample;

performing at least one of an intensity distribution analysis and an image subtraction analysis on the image collected from the measurement region.

33. The method of claim 32, wherein performing an intensity distribution analysis on the image collected from the measurement region comprises:

producing a reference intensity distribution for a reference sample that has no residue;

producing an intensity distribution for the image of the measurement region on the sample;

comparing the intensity distribution for the image to the reference intensity distribution; and determining that residue is present on the measurement region when the comparison between the intensity distribution for the image to the reference intensity distribution exceeds a predetermined threshold.

34. The method of claim 32, wherein performing image subtraction analysis on the image collected from the measurement region comprises:

producing a reference image for a reference sample that has no residue;

subtracting the image of the measurement region from the reference image;

converting the subtracted image to a binary image; and calculating the percentage of residue from the binary image.

35. The method of claim 26, wherein the thickness of the residue at the measurement region is quantitatively determined.

36. The method of claim 26, wherein the residue on the sample is produced by the incomplete removal of at least one of a barrier layer and a top layer that overlies the barrier layer, and wherein using the measured monitoring parameter and the calibration metric to determine the thickness of the residue determines the thickness of the incompletely removed at least one of the barrier layer and the top layer.

37. A method of characterizing residue on a sample, wherein the residue on the sample is produced by the incomplete removal of at least one of a barrier layer and a top layer that overlies the barrier layer, the method comprising:

collecting a reflectance spectrum for a measurement region on a sample;

performing spectral analysis on the reflectance spectrum collected from the measurement region, wherein the spectral analysis comprises measuring a monitoring parameter for the collected reflectance spectrum, wherein the spectral analysis uses a calibration metric that correlates the monitoring parameter to the thickness of the barrier layer and the thickness of the top layer; and using the measured monitoring parameter with the calibration metric to quantitatively determine the thickness of the incompletely removed at least one of the barrier layer and the top layer; and recording the results of the determined thickness.

38. The method of claim 37, wherein the monitoring parameter is one of a reflectance value at one or more of a local minima and maxima in the reflectance spectrum, a shape of one or more of the local minima and maxima in the reflectance spectrum, and a difference in reflectance values between at least two of the local minima and maxima in the reflectance spectrum.

39. The method of claim 37, wherein the calibration metric is at least one of a calibration look-up table that correlates a number of values for the monitoring parameter to the thickness of the barrier layer and the thickness of the top layer and one or more calibration equations that correlates the monitoring parameter to the thickness of the barrier layer and the thickness of the top layer.

40. The method of claim 37, further comprising:

collecting an image for the measurement region on the sample;

performing an image analysis of the image collected from the measurement region as a result of the spectral analysis indicating that residue is not present; and recording the results of the image analysis on the sample.

41. The method of claim 40, wherein performing an image analysis comprises:

performing an image analysis of an intensity distribution analysis on the image collected from the measurement region when the spectral analysis does not indicate that residue is present; and performing an image subtraction analysis on the image collected from the measurement region when the intensity distribution analysis does not indicate that residue is present.

* * * * *